United States Patent
Li et al.

(10) Patent No.: US 10,467,591 B2
(45) Date of Patent: Nov. 5, 2019

(54) SYSTEM AND METHOD FOR DETECTING SUBSTRATE AND MANUFACTURING DEVICE

(71) Applicant: BOE TECHNOLOGY GROUP CO., LTD., Beijing (CN)

(72) Inventors: Wusheng Li, Beijing (CN); Zhengliang Li, Beijing (CN); Zhen Liu, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 251 days.

(21) Appl. No.: 15/521,976

(22) PCT Filed: Oct. 21, 2016

(86) PCT No.: PCT/CN2016/102951
§ 371 (c)(1),
(2) Date: Apr. 26, 2017

(87) PCT Pub. No.: WO2017/118160
PCT Pub. Date: Jul. 13, 2017

(65) Prior Publication Data
US 2018/0090396 A1    Mar. 29, 2018

(30) Foreign Application Priority Data
Jan. 4, 2016  (CN) .......................... 2016 1 0005515

(51) Int. Cl.
*G01N 21/00* (2006.01)
*G06Q 10/10* (2012.01)
*G06F 8/65* (2018.01)

(52) U.S. Cl.
CPC .............. *G06Q 10/10* (2013.01); *G06F 8/65* (2013.01)

(58) Field of Classification Search
CPC .... G01N 21/94; G01N 21/9501; G01N 21/47; G01N 21/8806; G01N 21/956
(Continued)

(56) References Cited

U.S. PATENT DOCUMENTS 5,742,386 A * 4/1998 Nose .................. G01N 21/4738
356/237.2
6,528,333 B1  3/2003 Jun et al.
(Continued)

FOREIGN PATENT DOCUMENTS

CN    101082778 A    12/2007
CN    103680078 A     3/2014
(Continued)

OTHER PUBLICATIONS

Search Report and Written Opinion dated Jan. 20, 2017 from State Intellectual Property Office of the P.R. China.
First Chinese Office Action dated Nov. 3, 2017.

*Primary Examiner* — Md M Rahman
(74) *Attorney, Agent, or Firm* — Dilworth & Barrese, LLP.; Michael J. Musella, Esq.

(57) ABSTRACT

A system and a method for detecting a substrate and a manufacturing device are disclosed. The detection system includes: an emitting unit and a control unit; wherein the emitting unit provides a first reference light and a second reference light, the first reference light propagates to the control unit, the second reference light is modulated by the substrate to generate a test light, the test light propagates to the control unit; the control unit obtains and compares a power of the first reference light and a power of the test light so as to determine whether a foreign matter is present on a surface of the substrate. The detection system can prevent foreign matters such as photoresist from influencing other manufacturing devices such as cleaning and deposition
(Continued)

devices, which is beneficial to the maintenance and service of the manufacturing devices.

19 Claims, 4 Drawing Sheets

(58) Field of Classification Search
USPC ........................................................ 356/237.3
See application file for complete search history.

(56) References Cited

U.S. PATENT DOCUMENTS

| | | | | |
|---|---|---|---|---|
| 2002/0148738 | A1* | 10/2002 | Boyd | G01N 33/32 205/782 |
| 2004/0042014 | A1* | 3/2004 | Feldman | G01N 21/8851 356/484 |
| 2005/0043894 | A1* | 2/2005 | Fernandez | A61B 5/0215 702/19 |
| 2007/0154211 | A1 | 7/2007 | Kim | |
| 2009/0177094 | A1* | 7/2009 | Brown | A61B 5/0066 600/476 |
| 2010/0128276 | A1* | 5/2010 | De Groot | G01B 11/2441 356/450 |
| 2010/0198365 | A1* | 8/2010 | Kawabata | G01S 7/4812 700/12 |
| 2011/0102805 | A1* | 5/2011 | Kuramoto | G01B 9/02007 356/493 |
| 2012/0097099 | A1* | 4/2012 | Roeckle | B65G 49/0459 118/423 |
| 2013/0003152 | A1* | 1/2013 | Belousov | G01B 11/162 359/9 |
| 2017/0184495 | A1* | 6/2017 | Wu | B07C 1/00 |

FOREIGN PATENT DOCUMENTS

| | | |
|---|---|---|
| CN | 104022053 A | 9/2014 |
| CN | 105655267 A | 6/2016 |
| JP | 2000009655 A | 1/2000 |
| KR | 100738809 B1 | 7/2007 |

\* cited by examiner

SYSTEM AND METHOD FOR DETECTING SUBSTRATE AND MANUFACTURING DEVICE

FIELD OF THE ART

Embodiments of the disclosure relate to the field of display technologies, more particularly, to a system and method for detecting a substrate, and a manufacturing device.

BACKGROUND

Currently, in the field of semiconductor fabrication, especially in the field of liquid crystal panel fabrication, a cleaning device and a deposition device are indispensable devices for array processes, pre-clean processes and deposition (Dep) processes.

Cleaning is needed before the array and Dep processes, for the purpose of removing impurities, on a surface of a substrate, with physiochemical properties and electrical properties which may affect film formation, as well as dust, oil and natural oxidant attached to the surface of the substrate, so as to expose clean films and pure texture. However, some foreign matters may easily block filters in the cleaning device when being washed off. For example, photoresist residuals or unpeeled photoresist may be present on the substrate after an etching process. When such a substrate enters the cleaning device for cleaning, a large amount of photoresist may be cleaned, which over a long time may block the filters. Moreover, when the substrate enters a deposition device for deposition, no matter sputtering or Plasma Enhanced Chemical Vapor Deposition (PECVD) is used, an operation chamber of the deposition will always be contaminated due to the bombing of foreign matters such as photoresist by plasmas. As a result, the cleaning device has to be halted due to blocking of filters, and the deposition device has to be halted due to contamination of the operation chamber, thereby reducing the utilization of the devices.

SUMMARY

Embodiments of the disclosure provide a system and method for detecting a substrate, and a manufacturing device, which can give an alert in time by detecting foreign matters on the substrate.

According to first aspect of the disclosure, it is provided a detection system for detecting a substrate, comprising an emitting unit and a control unit, wherein the emitting unit is configured for providing a first reference light and a second reference light, the first reference light propagates to the control unit, the second reference light is modulated by the substrate to generate a test light, the test light propagates to the control unit; and the control unit is configured for obtaining and comparing a power of the first reference light and a power of the test light so as to determine whether a foreign matter is present on a surface of the substrate.

According to second aspect of the disclosure, it is provided a manufacturing device comprising the above detection system.

According to third aspect of the disclosure, it is provided a detection method for detecting a substrate, comprising: providing a first reference light and a second reference light, the second reference light is modulated by the substrate to generate a test light; obtaining and comparing a power of the first reference light and a power of the test light so as to determine whether a foreign matter is present on a surface of the substrate.

BRIEF DESCRIPTION OF THE DRAWINGS

In order to clearly illustrate the technical solution of the embodiments of the invention, the drawings of the embodiments will be briefly described in the following; it is obvious that the described drawings are only related to some of embodiments of the invention and thus are not limitative of the invention.

DETAILED DESCRIPTION

In order to make objects, technical details and advantages of the embodiments of the invention apparent, the technical solutions of the embodiments will be described in a clearly and fully understandable way in connection with the drawings related to the embodiments of the invention. Apparently, the described embodiments are just a part but not all of the embodiments of the invention. Based on the described embodiments herein, those skilled in the art can obtain other embodiment(s), without any inventive work, which should be within the scope of the invention.

Figure 1:
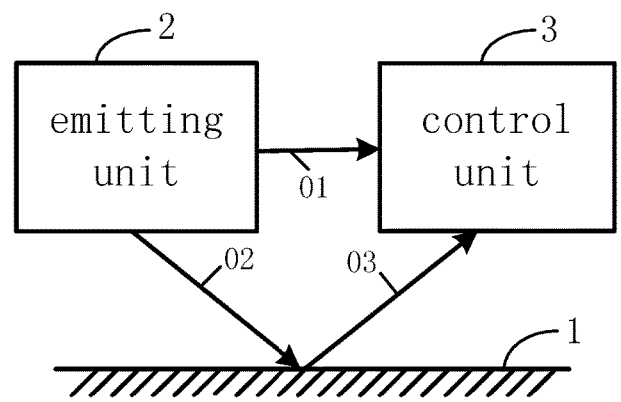
FIG. 1 is a schematic view of a detection system in accordance with an embodiment of the invention.

An embodiment of the disclosure provides a detection system for detecting a substrate 1 as illustrated in FIG. 1. The system comprises: an emitting unit 2 and a control unit 3. Herein the emitting unit 2 is configured for providing a first reference light 01 and a second reference light 02, the first reference light 01 propagates to the control unit 3, the second reference light 02 is modulated by the substrate 1 to generate a test light 03, the test light 03 propagates to the control unit 3. The control unit 3 is configured for obtaining a power of the first reference light 01 and a power of the test light 03, and comparing the power of the first reference light 01 and the power of the test light 03, so as to determine whether a foreign matter is present on a surface of the substrate 1, based on the comparison result.

It is noted that the foreign matters on the surface of the substrate may be some foreign matters which may easily block filters of a cleaning device or may easily contaminating a deposition device, such as photoresist. The term "Modulation" as used herein includes but is not limited to transmission and/or reflection of incident light by the substrate. The term "the surface of a substrate" as used herein refers to an outermost surface of a substrate. For example, when no layer is disposed on the substrate, "the surface of the substrate" refers to a surface of the substrate itself. When one or more films are disposed on the substrate, "the surface of the substrate" refers to a surface of the outermost film.

In at least some of embodiments, when determining that a foreign matter is present on the surface of the substrate 1, the control unit 3 generates an alert.

The detection system provided by the above embodiment of the disclosure can not only detect presence of foreign matters on the surface of the substrate, but also give an alert with regards to the presence of foreign matters on the surface of the substrate. In array processes, for example before a pre-clean process or a Dep-process, a timely alert can prevent foreign matters such as photoresist from influencing other manufacturing devices such as cleaning and deposition devices, which is beneficial to the maintenance and service of the manufacturing devices.

Figure 2:
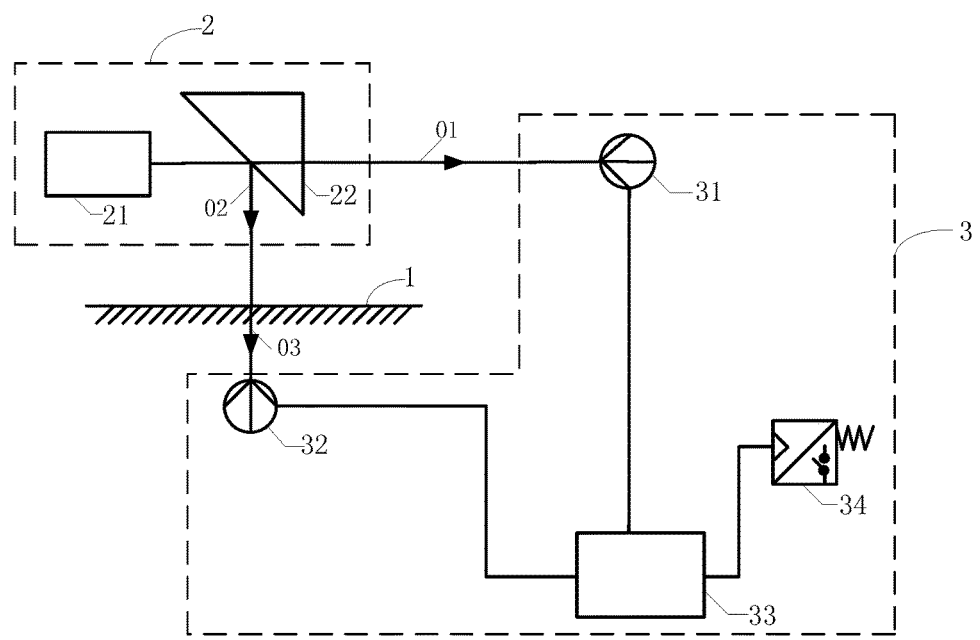
FIG. 2 is a schematic view of a detection system in accordance with another embodiment of the invention.
Figure 4:
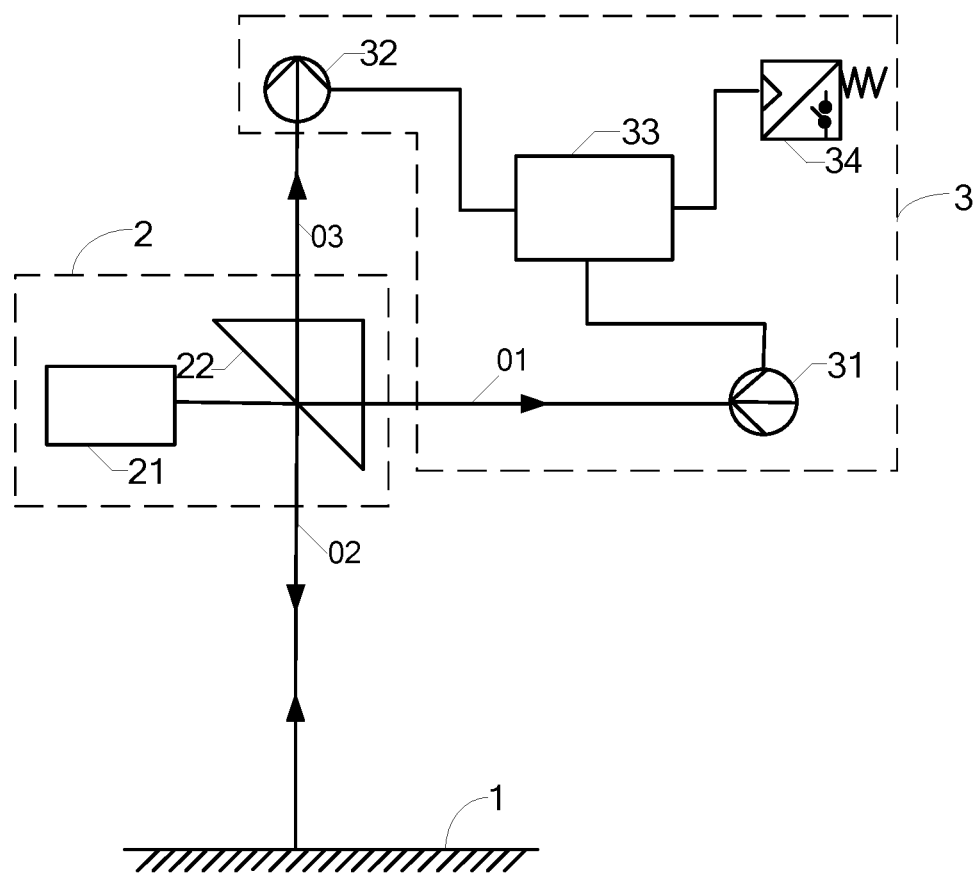
FIG. 4 is a schematic view of a detection system in accordance with still another embodiment of the invention.

In at least some of embodiments, as illustrated in FIGS. 2 and 4, the emitting unit 2 comprises a laser emitter 21 for emitting a laser beam, and a beam splitter 22 arranged on a transmission path of the laser beam, where the beam splitter 22 is configured for splitting the laser beam into the first reference light 01 and the second reference light 02. The first reference light 01 propagates to the control unit 3, the second reference light 02 propagates to a surface of the substrate 1 and is modulated by the substrate 1 to generate a test light 03, which is used to detect whether foreign matters are present on the surface of the substrate. As an example, the first reference light 01 may be used as a comparison basis of the test light 03, to detect power change of the light after passing through the surface of the substrate 1.

It is noted that transmission directions, powers and wavelengths of the first reference light 01 and the second reference light 02 formed by the beam splitter 22 may be configured according to a structure of the beam splitter 22. A beam splitter with any structure may compute in advance a relationship between powers of the formed first reference light 01 and second reference light 02, which may be used to generate computation reference values for the test light.

In at least some of embodiments, for the convenience of numerical computation, as illustrated in FIGS. 2 and 4, the beam splitter is a half-reflecting mirror. Based on the principle of the half-reflecting mirror, the generated first reference light 01 and second reference light 02 have the same power. As an example, after split by the half-reflecting mirror, transmission directions of the first reference light 01 and the second reference light 02 are perpendicular to each other.

In at least some of embodiments, as illustrated in FIGS. 2 and 4, the control unit 3 comprises: a first power sensor 31, a second power sensor 32, a controller 33 and an alarm 34. Herein, the first power sensor 31 is configured for receiving the first reference light 01 and calculating the power of the first reference light 01; the second power sensor 32 is configure for receiving the test light 03 and calculating the power of the test light 03; the controller 33 is configured for comparing the power of the first reference light 01 and the power of the test light 03 to obtain a test ratio; the alarm 34 is configured for giving an alert when it determines that a foreign matter is present on the surface of the substrate 1 based on the test ratio. The alarm may comprise at least one of an audio and visual signal. At this time, the manufacturing device may be halted to remind the staff to conduct inspection.

It is noted that the first power sensor and the second power sensor may be a laser energy meter, a laser power meter or other devices, as long as the powers of the first and second reference lights may be calculated, which will not be specifically defined here.

In at least some of embodiments, the controller 33 respectively receives data signals from the first power sensor 31 and the second power sensor 32 and obtains a test ratio after comparison. The alarm 34 then receives the test ratio. When it is determined that the test ratio is larger than a predetermined value, the alarm 34 makes a decision that foreign matters are present on the surface of the substrate and gives an alert.

It is noted that the predetermined value (e.g. of 2 or 5) that the presence of foreign matters on the surface of the substrate will cause device fault may be set in advance based on experience over time by the staff. When the alarm determines that the obtained test ratio is larger than the predetermined value, it gives an alert. The predetermined value may be different dependent on the modulation (e.g. reflection or transmission) of the lights by the film on the surface the substrate.

In at least some of embodiments, as illustrated in FIG. 2, when a light-transmissive film is disposed on the surface of the substrate 1, the test light 03 is a transmitted light generated after the second reference light 02 is transmitted through the light-transmissive film on the surface of the substrate; the second power sensor 32 is located on the transmission path of the transmitted light, which means the second power sensor 32 is disposed behind the substrate 1 to receive the transmitted light.

It is noted that the light-transmissive film may be non-metal film, such as a passivation layer, an insulation layer, or other films which may be light-transmitted, such as a transparent conductive layer, which will not be defined here. In this case, the predetermined value may be set to 5. When the alarm determines that the test ratio is larger than 5, it gives an alert.

Another embodiment of the disclosure further provides a detection method for detecting a substrate, comprising:

providing a first reference light and a second reference light, the second reference light is modulated by the substrate to generate a test light;

obtaining and comparing a power of the first reference light and a power of the test light so as to determine whether a foreign matter is present on a surface of the substrate.

In at least some of embodiments, the above method further comprises: giving an alert when determining that a foreign matter is present on the surface of the substrate.

In at least some of embodiments, the above method further comprises: comparing the power of the first reference light and the power of the test light to obtain a test ratio, and determining that a foreign matter is present on the surface of the substrate when the test ratio is larger than a predetermined value, and giving an alert.

In at least some of embodiments, the above method is performed by the detection device of any of the above embodiments. As an example, the method comprises:

emitting a laser beam by a laser emitter, splitting the laser beam into a first reference light and a second reference light, wherein the first reference light propagates to a control unit, the second reference light propagates to a surface of the substrate;

modulating the second reference light into a test light by the surface of the substrate, and propagating the test light to the control unit;

comparing a power of the first reference light with a power of the test light, and determining whether a foreign matter is present on the surface of the substrate based on a comparison result.

Figure 3:
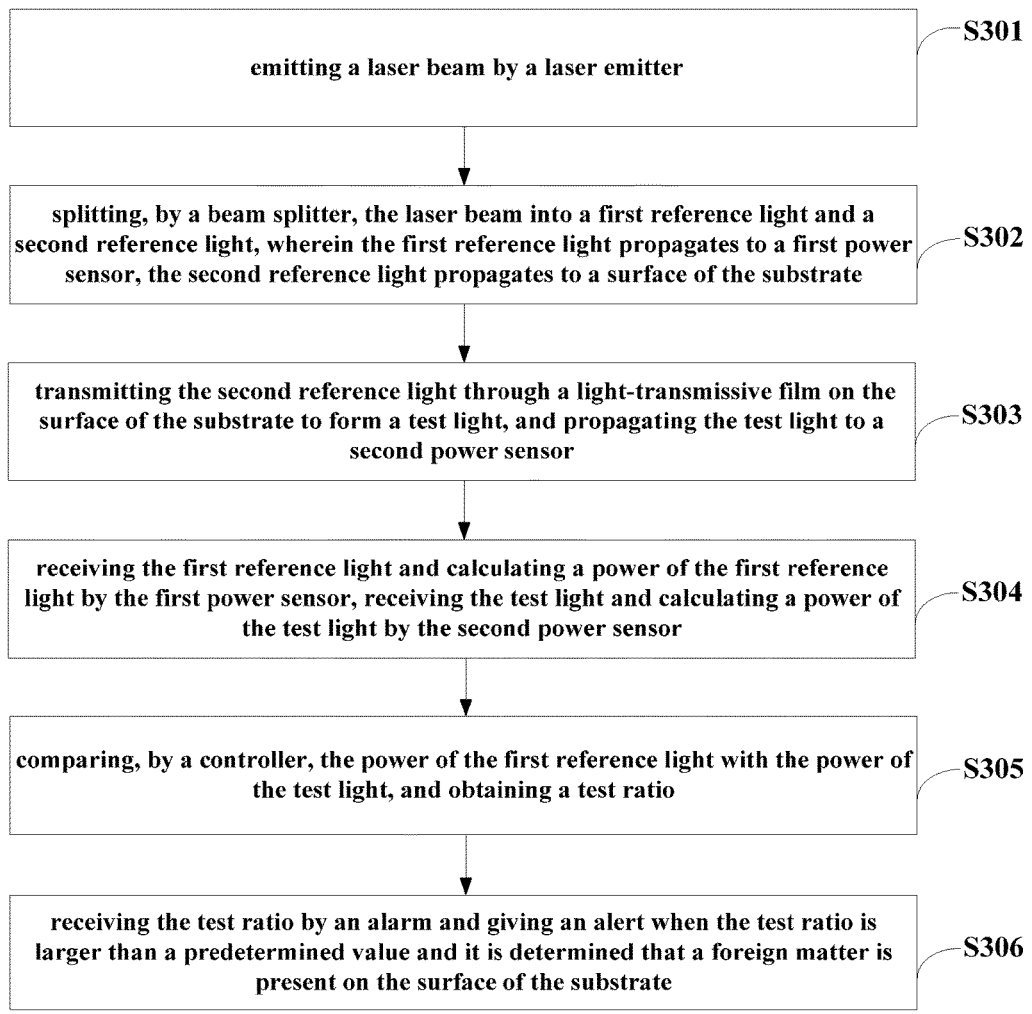
FIG. 3 schematically illustrates an operation flow chart of the detection system of FIG. 2.

As an example, the detection system as illustrated in FIG. 2 is used to detect a substrate, the detection method as illustrated in FIG. 3 comprises:

S301, emitting a laser beam by a laser emitter,

S302, splitting, by a beam splitter, the laser beam into a first reference light and a second reference light, wherein the first reference light propagates to a first power sensor, the second reference light propagates to a surface of the substrate;

S303, transmitting the second reference light through a light-transmissive film on the surface of the substrate to form a test light, and propagating the test light to a second power sensor;

S304: receiving the first reference light and calculating a power of the first reference light by the first power sensor, receiving the test light and calculating a power of the test light by the second power sensor;

S305, comparing, by a controller, the power of the first reference light with the power of the test light, and obtaining a test ratio;

S306, receiving the test ratio by an alarm and giving an alert when the test ratio is larger than a predetermined value and it is determined that a foreign matter is present on the surface of the substrate.

As an example, when a reflective film is disposed on the surface of the substrate, the test light is a reflected light generated after the second reference light is reflected by the reflective film on the surface of the substrate; the second power sensor is located on the transmission path of the reflected light. That is, the second power sensor is placed in front of the substrate so as to receiving the reflected light, as long as the second reference light is not shielded.

It is noted that the above reflective film may be a metal film, such as a gate electrode, a source/drain electrode, or other films which may reflect light, such as a black matrix layer, which will not be defined here.

As another example illustrated in FIG. 4, when a reflective film is disposed on the surface of the substrate 1, the second reference light 02 incidents on the surface of the substrate 1 vertically, the second reference light 02 is reflected by the reflective film on the surface of the substrate 1 and then passes through the emitting unit 2 to form the test light 03; the second power sensor 32 is located on the transmission path of the transmitted light, i.e., the test light 03. That is, the second power sensor 32 is placed in front of the substrate so as to receiving the transmitted light.

As illustrated in FIG. 4, it is noted that the beam splitter 22 in the emitting unit 2 receives the light reflected by the surface of the substrate 1, which is split again by the beam splitter 22 to generate a transmitted light. The transmitted light functions as the test light 03 and propagates to the control unit 3. The reflective film may be a metal film, such as a gate electrode, a source/drain electrode, or other films which may reflect light, such as a black matrix layer, which will not be defined here. The predetermined value may be set to 2. When the alarm determines that the obtained test ratio is larger than 2, an alert will be given.

Figure 5:
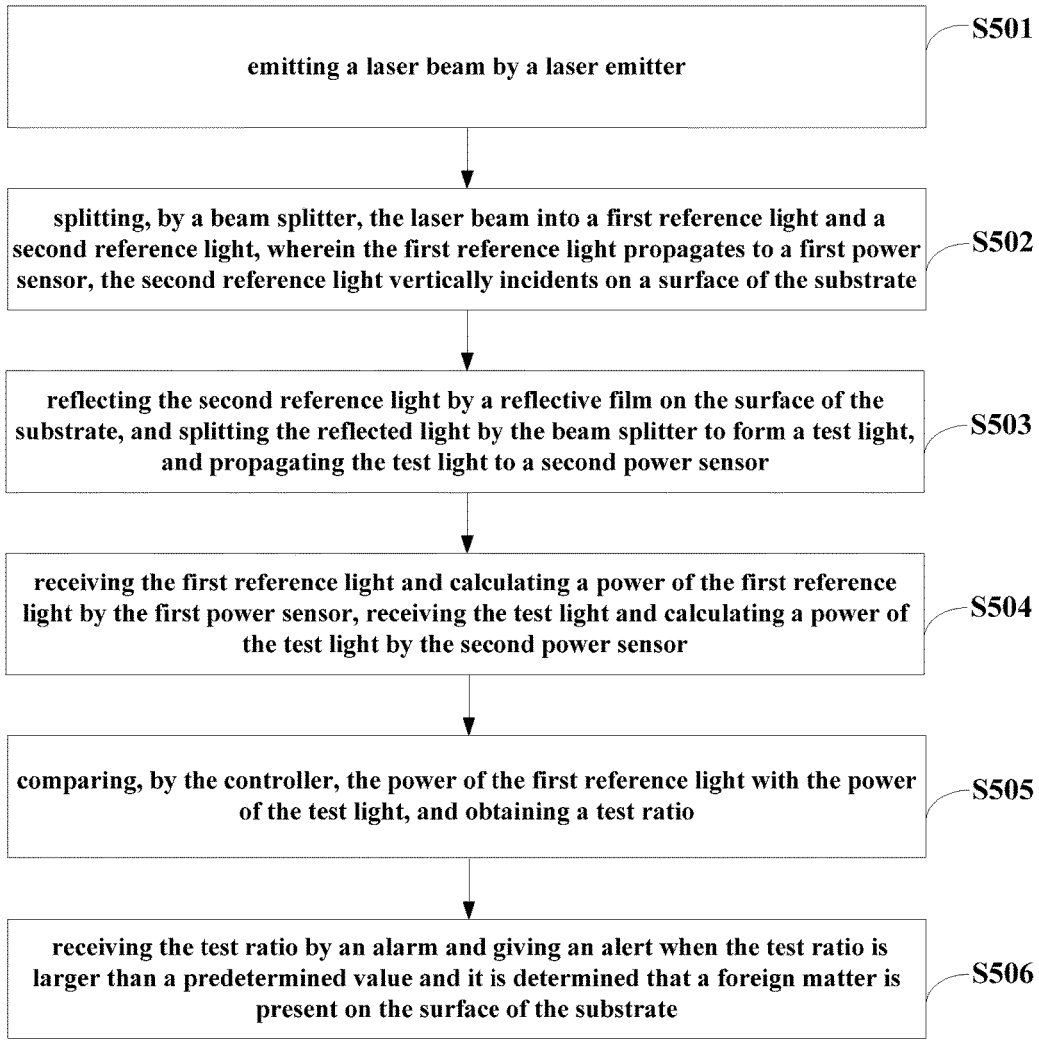
FIG. 5 schematically illustrates an operation flow chart of the detection system of FIG. 4.

As an example, the detection system as illustrated in FIG. 4 is used to detect a substrate, the detection method as illustrated in FIG. 5 comprises:

S501, emitting a laser beam by a laser emitter,

S502, splitting, by a beam splitter, the laser beam into a first reference light and a second reference light, wherein the first reference light propagates to a first power sensor, the second reference light vertically incidents on a surface of the substrate;

S503, reflecting the second reference light by a reflective film on the surface of the substrate, and splitting the reflected light by the beam splitter to form a test light, and propagating the test light to a second power sensor;

S504: receiving the first reference light and calculating a power of the first reference light by the first power sensor, receiving the test light and calculating a power of the test light by the second power sensor;

S505, comparing, by the controller, the power of the first reference light with the power of the test light, and obtaining a test ratio;

S506, receiving the test ratio by an alarm and giving an alert when the test ratio is larger than a predetermined value and it is determined that a foreign matter is present on the surface of the substrate.

As an example, in order to make the loss in the optical path the same, a sum of a length of optical path of the second reference light and a length of optical path of the test light is equal to a length of optical path of the first reference light, which helps to further increase the accuracy of the alarm.

As another example, the substrate is a substrate to be cleaned and disposed in a cleaning device, or a substrate to be deposited and disposed in a deposition device.

Still another embodiment of the invention further provides a manufacturing device, which comprises the detection system of any of the above embodiments. The manufacturing device may be a cleaning device, a deposition device or other devices. It is note that the detection system may be arranged at an inlet of the cleaning or deposition device, to detect and alert before cleaning or depositing a substrate. Other necessary parts of the manufacturing device are known to a person skilled in the art, which will not be elaborated here and should not be construed as being limitative to the disclosure.

In the detection system and manufacturing device provided by the above embodiments of the disclosure, it can determine whether there is foreign matters on the surface of the substrate based on change of test light, thereby giving an alert. It thus prevents foreign matters such as photoresist from influencing other manufacturing devices such as the cleaning or deposition device, which is beneficial to the maintenance and service of the manufacturing devices.

What is described above is related to the illustrative embodiments of the disclosure only and not limitative to the scope of the disclosure; the scopes of the disclosure are defined by the accompanying claims.

The present application claims priority from Chinese Application No. 201610005515.X, filed on Jan. 4, 2016, the disclosure of which is incorporated herein by reference in its entirety

What is claimed is:

1. A detection system for detecting a substrate, comprising an emitter and a controller unit, wherein
the emitter is configured for providing a first reference light and a second reference light, the first reference light propagates to the controller unit, the second reference light is modulated by the substrate to generate a test light, and the test light propagates to the controller unit; and
the controller unit is configured for obtaining and comparing a power measured in watts of the first reference light and a power measured in watts of the test light so as to determine whether a foreign matter is present on a surface of the substrate,
wherein the second reference light entering the substrate from the surface of the substrate leaves the substrate from an outer surface that is comprised by the substrate and is opposite to the surface of the substrate, and then is received by the controller unit.

2. The detection system of claim 1, wherein the controller unit is configured for giving an alert when the controller unit determines that a foreign matter is present on the surface of the substrate.

3. The detection system of claim 1, wherein the emitter comprises a laser emitter for emitting a laser beam, and a beam splitter which is arranged on a transmission path of the laser beam and configured for splitting the laser beam into the first reference light and the second reference light; and
the first reference light directly formed due to a slitting function of the beam splitter is directly received by the controller unit.

4. The detection system of claim 3, wherein the beam splitter is a half-reflecting mirror.

5. The detection system of claim 3, wherein the power measured in watts of the first reference light is the same as that of the second reference light.

6. The detection system of claim 1, wherein the controller unit comprises a first power sensor, a second power sensor, a controller and an alarm, wherein,
the first power sensor is configured for receiving the first reference light and calculating the power measured in watts of the first reference light;
the second power sensor is configured for receiving the test light and calculating the power measured in watts of the test light;
the controller is configured for comparing the power measured in watts of the first reference light and the power measured in watts of the test light to obtain a test ratio;
the alarm is configured for giving an alert when it determines that the foreign matter is present on the surface of the substrate based on the test ratio.

7. The detection system of claim 6, wherein in condition that the test ratio is larger than a predetermined value, the alarm determines that the foreign matter is present on the surface of the substrate and gives the alert.

8. The detection system of claim 6, wherein a light-transmissive film is disposed on the surface of the substrate,
the test light is a transmitted light generated after the second reference light is transmitted through the light-transmissive film on the surface of the substrate;
the second power sensor is disposed on the transmission path of the transmitted light.

9. The detection system of claim 6, wherein a reflective film is disposed on the surface of the substrate,
the test light is a reflected light generated after the second reference light is reflected by the reflective film on the surface of the substrate;
the second power sensor is located on the transmission path of the reflected light.

10. The detection system of claim 6, wherein a reflective film is disposed on the surface of the substrate,
the test light is a transmitted light generated after the second reference light incidents on the surface of the substrate and is reflected by the reflective film on the surface of the substrate and then passes through the emitter;
the second power sensor is disposed on the transmission path of the transmitted light.

11. The detection system of claim 1, wherein a sum of optical path lengths of the second reference light and the test light is equal to an optical path length of the first reference light.

12. The detection system of claim 1, wherein the substrate is a substrate to be cleaned and disposed in a cleaning device.

13. The detection system of claim 1, wherein the substrate is a substrate to be deposited and disposed in a deposition device.

14. A manufacturing device comprising the detection system of claim 1.

15. The manufacturing device of claim 14, wherein the manufacturing device is a cleaning device.

16. The manufacturing device of claim 14, wherein the manufacturing device is a deposition device.

17. A detection method for detecting a substrate, comprising:
providing a first reference light and a second reference light, the second reference light is modulated by the substrate to generate a test light;
obtaining and comparing a power measured in watts of the first reference light and a power measured in watts of the test light so as to determine whether a foreign matter is present on a surface of the substrate,
wherein the second reference light entering the substrate from the surface of the substrate leaves the substrate from an outer surface that is comprised by the substrate and is opposite to the surface of the substrate, and then is received by the controller unit.

18. The detection method of claim 17, further comprising: giving an alert when determining that the foreign matter is present on the surface of the substrate.

19. The detection method of claim 18, further comprising: comparing the power measured in watts of the first reference light and the power measured in watts of the test light to obtain a test ratio, and giving an alert when the test ratio is larger than a predetermined value and determining that the foreign matter is present on the surface of the substrate.

* * * * *